United States Patent [19]

Morozowich

[11] 4,005,133
[45] Jan. 25, 1977

[54] PGF$_{2\alpha}$, L-ARGININE SALT

[75] Inventor: Walter Morozowich, Kalamazoo Township, Kalamazoo County, Mich.

[73] Assignee: The Upjohn Company, Kalamazoo, Mich.

[22] Filed: Oct. 14, 1975

[21] Appl. No.: 622,129

[52] U.S. Cl. .......................... 260/501.11; 424/316
[51] Int. Cl.$^2$ ...................................... C07C 101/24
[58] Field of Search ............................. 260/501.11

[56] References Cited
UNITED STATES PATENTS

| | | | |
|---|---|---|---|
| 3,706,789 | 12/1972 | Bergstrom et al. | 260/501.1 |
| 3,872,107 | 3/1975 | Crabbe | 260/501.11 |
| 3,931,282 | 1/1976 | Muchowski et al. | 260/501.11 |
| 3,931,297 | 1/1976 | Crabbe | 260/501.11 |

Primary Examiner—James O. Thomas, Jr.
Assistant Examiner—G. T. Breitenstein
Attorney, Agent, or Firm—Robert A. Armitage

[57] ABSTRACT

PGF$_{2\alpha}$, L-arginine salt is disclosed with a process for preparing a free-flowing solid form thereof. Further, the preparation and use of this salt in regulation of the estrus of domestic animals is described.

2 Claims, No Drawings

PGF$_{2\alpha}$, L-ARGININE SALT

DESCRIPTION OF THE INVENTION

The present invention embodies the surprising and unexpected discovery that a novel composition of matter, the L-arginine salt of PGF$_{2\alpha}$, is highly useful as a regulator of the estrus in domestic animals. Further, the present invention comprises the surprising and unexpected discovery of a novel process which is useful in preparing a free-flowing water-soluble solid form of PGF$_{2\alpha}$, L-arginine salt. This solid form is conveniently and readily adaptable for preparing injectable formulations of PGF$_{2\alpha}$, L-arginine salt.

PGF$_{2\alpha}$ and certain of its metal, ammonium, amine, and quaternary ammonium salts are known in the art to be potent pharmacological agents, as, for example, is described in U.S. Pat. No. 3,706,789. Additionally, free-flowing crystalline solid salts of PGF$_{2\alpha}$ are likewise known to be similarly useful pharmacological agents as is described in U.S. Pat. No. 3,703,544. Finally other amine salts of PGF$_{2\alpha}$ are described in U.S. Pat. Nos. 3,673,213; 3,845,111; and 3,708,492.

Certain basic amino acid salts of carboxylic acids are known in the art. For example the L-arginine and L-lysine salts of certain prostanoic acid derivatives are generally described in U.S. Pat. No. 3,872,107, German Offenlegungschrift 2,355,324 (Derwent Farmdoc CPI 40258V) and Belgian Pat. No. 807,385 (Derwent Farmdoc CPI 39929V).

Finally, the use of the THAM salt of PGF$_{2\alpha}$ in the regulation of the estrus of domestic animals is known in the art. See, for example Lauderdale, J. W., J. Anim. Sci. 35:426 (1972); Lauderdale, J. W., et al., J. Anim, Sci. 38:964 (1974); Miller, R. A., et al., J. Anim. Sci. 41:369 (1975); and Hafez, Ed., Reproduction of Farm Animals, 3rd. Edition, Lea and Febizer, (1974), pp. 432–436 and references cited therein which describe method of administration and the effect of subcutaneous or intramuscular injection of the tris(hydroxyamino)-methane (THAM) salt of PGF$_{2\alpha}$ on the estrus cycle of domestic animals and discuss the desirability and usefulness of such activity.

In preparing the novel L-arginine salt of PGF$_{2\alpha}$ for use in estrus regulation, it is highly desirable to obtain this salt first as a free-flowing, water-soluble solid, so as to facilitate later handling, weighing, and other aspects of pharmacological formulation. Accordingly, the present invention provides a novel method for recovery of PGF$_{2\alpha}$ L-arginine salt as a free-flowing, water-soluble solid.

The novel process for preparing the L-arginine salt of PGF$_{2\alpha}$ and thereafter recovering this salt as a free-flowing, water soluble solid comprises:

1. (a) contacting PGF$_{2\alpha}$ and L-arginine in a polar organic solvent or (b) dissolving a PGF$_{2\alpha}$ salt in a mixture of water and a polar organic solvent and passing the resulting solution through an ion exchange resin charged with L-arginine, thereby preparing a solution containing the L-arginine salt of PGF$_{2\alpha}$; and
2. recovering by precipitation with a non-solvent a free-flowing solid form of the salt of step 1.

Examples of polar organic solvents useful in the above process are the lower alkanols, e.g., methanol, ethanol, the propanols, or the butanols; amides, e.g., dimethylformamide; or other relatively polar organic compounds (e.g., 1,2-dimethoxyethane, dimethylsulfoxide, or tetrahydrofuran).

The first step of the process described above, the preparation of the L-arginine salt of PGF$_{2\alpha}$ in solution, is achieved by one of several methods.

By a first method a known salt of PGF$_{2\alpha}$, such as the sodium salt, triethylamine salt or the like, is passed through an ion exchange charged with cations of L-arginine thereby forming the L-arginine salt. For this purpose a suitable solvent medium is water in combination with a lower alkanol (e.g., methanol or ethanol) or a polar organic solvent as above.

Those ion-exchange resins which are useful in the present process are cation exchangers with phenolic-, polystyrene-, or acrylic-type resins evidencing sulfonic, phosphoric or carboxylic acid moieties. In addition, a carboxymethylcellulose or sulfoethylcellulose or phenoethylcellulose may be employed as an ion-exchange support.

The salts of PGF$_{2\alpha}$ used herein on the resin are known or are readily prepared by conventional methods. For example the sodium salt is prepared by neutralization of PGF$_{2\alpha}$ with an equivalent of sodium hydroxide. The reaction is conveniently carried out in a water-alkanol solvent, facilitating direct use of the product on the resin.

By a second method the solution containg the L-arginine salt of PGF$_{2\alpha}$ is prepared by mixing PGF$_{2\alpha}$ and L-arginine with vigorous stirring. Preferred reaction solvents are the lower alkanols, although the polar organic solvents described above are also employed.

After preparation of the above solution of the L-arginine salt of PGF$_{2\alpha}$, the recovery of the salt as a free-flowing, water-soluble solid proceeds first by removal of substantially all water. Thus, for water-containing solutions the solvent is evaporated to dryness, followed by solution of the dried residue in a dry (water-free) or substantially dry, polar organic solvent as described above. For this purpose the preferred solvent is a lower alkanol. Thus there is prepared when either of the above methods is employed the PGF$_{2\alpha}$ L-arginine salt in a dry solution of a polar organic solvent. Thereafter the recovery of the salt proceeds by slow addition of the PGF$_{2\alpha}$, L-arginine salt solution to a large volume of an organic non-solvent (for PGF$_{2\alpha}$, L-arginine salt). For example, it is preferred to use 10–200 volumes of organic non-solvent for each volume of the PGF$_{2\alpha}$, L-arginine salt solution. The preferred organic non-solvent is acetonitrile, although other non-solvents, as would be apparent to one of ordinary skill in the art, are likewise useful. For example, chlorinated hydrocarbons (e.g., methylene chloride, carbontetrachloride, trichloroethylene, and tetrachloroethylene), hexane, benzene, or any substantially non-polar organic compound is a useful non-solvent, provided however that all non-solvents employed herein must be essentially miscible with the polar organic solvent selected above.

As a further aspect to the recovery, the slow addition of the salt solution to the organic non-solvent is optionally preceeded by addition of a small amount of the organic non-solvent to the salt solution. Care must be taken to avoid creation of turbid solutions or solutions with other undesirable physical characteristics (e.g., foam formation) and accordingly this addition should be limited to about an equal volume amount of non-solvent as polar organic solvent.

After addition to the organic non-solvent, preferably accompanied by gentle stirring, the product appears as a finely-divided precipitate, recoverable by conventional techniques (e.g., filtration).

The product of the above process though recovered as a white, free-flowing water soluble product may exhibit undesired changes in physical properties (e.g., loss of free-flowability) upon prolonged exposure to high atmospheric humidity. Accordingly, care to avoid such exposure is necessary to maintain optimal physical properties prior to and during formulation. Conventional techniques, e.g., storage in sealed containers, represent adequate protective techniques.

For formulation of the pharmacologically useful injectable form of the salt, the salt is optionally combined with required buffers and thereafter diluted to the desired concentration with water or saline solution. The desired pH range is 7-9, preferably being about 8.

The injectable formulation is then employed in regulation of the estrus by injection intermuscularly or subcutaneously of a solution containing 0.1 to 100 mg. of the $PGF_{2\alpha}$ anion, the exact dose depending on the size, type and weight of the animal being treated. See the references cited above for typical dosing schedules, methods of administration and effects of treatment.

The preparation of the solid free flowing form of $PGF_{2\alpha}$, L-arginine salt is described by the following example:

$PGF_{2\alpha}$ (2.143 gm.) and L-arginine (1.010 gm) are dissolved in 10 ml. of methanol with vigorous stirring. The resulting solution is diluted with 10 ml. of acetonitrile and then dripped into 500 ml. of acetonitrile with gentle stirring. A precipitate forms and is isolated by filtration under a nitrogen atmosphere. The filtrate is washed with acetonitrile, and dried with nitrogen for 30 min. to obtain 2.748 gm. of product. Melting point is 45.0°–55.1° C.

I claim:
1. $PGF_{2\alpha}$, L-arginine salt.
2. The free-flowing solid form of $PGF_{2\alpha}$, L-arginine salt.

* * * * *